(12) United States Patent
Lehmann et al.

(10) Patent No.: US 7,777,283 B2
(45) Date of Patent: Aug. 17, 2010

(54) ELECTRIC COMPONENT

(75) Inventors: Mirko Lehmann, Ebnat-Kappel (CH);
Ingo Freund, Ebnat-Kappel (CH)

(73) Assignee: Micronas GmbH, Freiburg i.Br (DE)

( * ) Notice: Subject to any disclaimer, the term of this patent is extended or adjusted under 35 U.S.C. 154(b) by 378 days.

(21) Appl. No.: 11/791,501

(22) PCT Filed: Nov. 26, 2004

(86) PCT No.: PCT/EP2004/013464

§ 371 (c)(1),
(2), (4) Date: May 24, 2007

(87) PCT Pub. No.: WO2006/056226

PCT Pub. Date: Jun. 1, 2006

(65) Prior Publication Data

US 2007/0290235 A1   Dec. 20, 2007

(51) Int. Cl.
*H01L 29/00* (2006.01)

(52) U.S. Cl. .................................. 257/414; 257/253

(58) Field of Classification Search .............. 257/253, 257/414, 758
See application file for complete search history.

(56) References Cited

U.S. PATENT DOCUMENTS

| | | | |
|---|---|---|---|
| 5,319,226 A | | 6/1994 | Sohn et al. |
| 5,944,970 A | * | 8/1999 | Rosenblatt ............. 204/416 |
| 7,061,061 B2 | * | 6/2006 | Goodman et al. .......... 257/414 |
| 2003/0107097 A1 | * | 6/2003 | McArthur et al. .......... 257/414 |
| 2006/0108219 A1 | * | 5/2006 | Kuroda et al. ............ 204/403.1 |

FOREIGN PATENT DOCUMENTS

| | | |
|---|---|---|
| DE | 3637513 | 5/1988 |
| DE | 19641777 | 4/1998 |
| EP | 0193251 | 9/1986 |
| WO | 02/01647 | 1/2002 |
| WO | 03/014722 | 2/2003 |

OTHER PUBLICATIONS

Faβbender et al., "Optimization of passivation layers for corrosion protection of silicon-based microelectrode arrays", 2000.

* cited by examiner

*Primary Examiner*—Allan R. Wilson
(74) *Attorney, Agent, or Firm*—The Webb Law Firm

(57) ABSTRACT

An electric component comprising a sensor and/or actuator chip with a substrate on which a passivating layer and a sensor and/or actuator structure consisting of an active surface area is arranged. The chip is surrounded by an encapsulation having an opening which forms an access to the at least one active surface area. A layer stack is arranged on the substrate, said stack of layers comprising from the passivating layer to the substrate at least one first strip conductor layer, a first electric insulating layer, a second strip conductor layer and a second electric insulating layer. The first conductor strip layer is fully arranged outside the area of the chip covered by the opening. At least one conductor strip of the second conductor strip layer is connected to the sensor and/or actuator structure.

6 Claims, 2 Drawing Sheets

ELECTRIC COMPONENT

BACKGROUND OF THE INVENTION

1. Field of the Invention

The invention relates to an electrical component having a sensor and/or actuator chip, in particular a CMOS chip, that has a substrate on which a passivation layer and at least one structure that has at least one active surface area for a sensor and/or actuator are located, and the chip is surrounded by an encapsulation that has at least one opening that forms an access to the active surface area, of which at least one is present, and to the passivation layer, and in the opening the chip has an interaction surface that extends, at least in some areas, over the passivation layer and the active surface area and that in the operating position is in contact with a liquid or viscous medium, and a first electrical insulation layer is provided between the passivation layer and the substrate, and a first conductor track layer is located in some areas between the passivation layer and the first insulation layer, and a second electrical insulation layer is provided between the first insulation layer and the substrate, and a second conductor track layer is located between the first insulation layer and the second insulation layer, and at least one of the conductor tracks is connected to the sensor and/or actuator structure.

2. Description of Related Art

An electrical component of this type is known from actual practice. It has a CMOS chip with a semiconductor substrate into which an ion-sensitive field effect transistor (ISFET) is integrated. The sensor has an active surface area that is configured as a gate electrode and that can be brought into contact with a liquid medium in order to detect ions contained in this medium. A plurality of conductor track layers made of aluminum, in which the conductor tracks and/or sections of conductor tracks extend, are located on the substrate. Conductor track sections of conductor tracks that extend across to a plurality of conductor track layers are connected to each other by means of through-contacts. An electrical insulation layer is provided between each of the conductor track layers as well as between the lowermost conductor track layer, which is located closest to the substrate, and the substrate. A passivation layer is located as a cover layer on the stack of layers comprising the conductor track layers and the insulation layers. The circuit tracks connect the drain and source of the ISFET with bond pads that are spaced apart from the drain and source and are located on the surface of the CMOS chip.

The CMOS chip is encapsulated with a plastic casting compound that is in close contact with the chip and that has an opening that is connected to the active surface area and into which the liquid medium may be filled. Thus, the medium [typo in German] comes into contact with the chip at an interaction surface that extends across a part of the passivation later and the active surface area. The conductor layers and the insulation layers in each case extend into the area of the chip that is covered by the interaction surface. The passivation layer and the insulation layers serve as corrosion protection for the circuit track layers in order to prevent the circuit track layers from coming into contact with the liquid medium. However, it has been found in actual practice that the passivation layer only provides limited corrosion protection for the conductor track layers, and that the chips only have a relatively short service life when the opening is filled with a liquid or viscous medium. If a conductor track comes into contact with the medium, for example due to a defect in the passivation layer, the entire chip can fail.

A semiconductor chip that has a silicon substrate on which an array having 16 approximately rectangular electrodes is disposed as disclosed in F. Faβbender et. al., Optimization of Passivation Layers for Corrosion Protection of Silicon-Based Microelectrode Arrays, Sensors and Actuators B 68 (2000), p. 128-133. The electrodes are connected to bond pads by means of conductor tracks located in a single conductor track layer. The conductor track layer is covered by a passivation layer. When the chip is manufactured, a silicon dioxide layer is generated on the semiconductor substrate with the aid of a heat-treating process. Trench-like recesses are imparted in this layer at the locations at which the conductor tracks will later be present. A metal that forms the circuit tracks is deposited in these recesses. The recessed arrangement of the conductor tracks in the silicon dioxide layer causes the chip to have an essentially flat surface. The purpose of these is to prevent mechanical stresses in the passivation layer, which can lead to cracks through which an analyte that is to be analyzed using the electrodes can come into contact with the conductor track layer and can cause corrosion on the conductor track layer. The corrosion resistance of the chip can be improved with this measure, and thus the service life of the chip can be extended. However, placing the trenches in the silicon dioxide layer located on the substrate results in a substantial additional expense in the manufacturing of the chip, in particular with a CMOS process.

The object of the invention is therefore to provide an electrical component of the type referred to above that can be manufactured in a cost-effective manner using the standard semiconductor manufacturing processes but that permits good corrosion resistance as well as long service life.

SUMMARY OF THE INVENTION

In the invention, at least those areas of the first conductor track layer adjacent to the passivation layer that carry an electrical potential or that are necessary for the electrical operation of the component are located completely outside of the area of the chip that is covered by the interaction surface. In the area of the chip that is covered by the interaction surface, in addition to the passivation layer at least the first insulation layer is then located between the uppermost conductor track layer that has the least distance to the opening or to the liquid or viscous medium contained in it and the conductor track layer that is used for the electrical operation of the component, whereby the corrosion resistance is significantly improved compared with a chip in which only the passivation layer is provided between the uppermost conductor track layer and the liquid or viscous medium. Inside of the area of the chip that is covered by the interaction surface, at least one electrically insulated, floating partial area of the first conductor track layer, which is not used to carry electrical voltage and/or current and therefore is not significant to the electrical operation of the component, may optionally be located. When the chip is manufactured, after the conductor track, of which there is at least one, of the second conductor track layer is produced, the first insulation layer is produced on or applied to the chip and after that the first conductor track layer and the passivation layer are produced on the chip or are applied to it. The surface structure caused by the contour of the conductor track, of which there is at least one, on the boundary surface of the insulation layer that is distant from the conductor track is already significantly flatter and smoother compared with the contour of the conductor track of the second conductor track layer. This surface structure is smoothed even more by the passivation layer, so that the passivation layer has a surface that is for the most part flat and free from abrupt steps or shoulders. This significantly reduces the risk that cracks will form in the passivation layer when mechanical stresses are present in the chip. The component of the invention therefore achieves good corrosion resistance and a long service life. The component chip can be manufactured economically using standard semiconductor manufacturing processes. Providing trenches in the chip surface, which is a complicated and expensive undertaking, is not necessary. The passivation layer may be comprised of a plurality of layers, each of which may be made of various materials. This results in even better corrosion protection. The electrical component may also be a gas sensor in which the liquid medium that comes into contact with the interaction surface is, for example, a 2-3-nanometer-thick moist layer.

In the invention, at least in the area of the first conductor track layer that is covered by the interaction surface, the distances between the electrically conductive layer areas of this conductor track layer that are laterally adjacent to each other and spaced apart from each other are in each case less than 1.2 times the thickness of the conductor track layer. This ensures in a simple way that the surface of the passivation layer that is located on the first conductor track layer and that in the operating position is in contact with the liquid or viscous medium is for the most part flat in the areas that cover the spacings between areas of the first conductor track layer. This significantly reduces the risk that cracks will form in the passivation layer went mechanical stresses are present in the chip. The electrical component of the invention therefore has good corrosion resistance and a long service life. The component chip can be manufactured economically using standard semiconductor manufacturing processes. The interaction surface that is provided for contact with the medium preferably extends across the entire surface area of the chip that is covered by the opening of the encapsulation.

In a preferred embodiment of the invention, the distances between the laterally adjacent areas of this conductor track layer in each case are less than 1.1 times the thickness of the first conductor track layer, in particular less than 1.0 times, possibly less than 0.9 times, and preferably less than 0.8 times this thickness, at the least in the area of the first conductor track layer covered by the interaction surface. In this case, the electric component makes even better corrosion resistance possible.

When the second conductor track layer has at least two electrically conducting layer areas that are laterally spaced apart from each other, it is advantageous if, at least in the area of the first conductor track layer covered by the interaction surface, the distances between the laterally adjacent areas of this circuit track layer are each less than 1.2 times the thickness of the second conductor track layer, in particular less than 1.1 times, in some cases less than 1.0 times, possibly less than 0.9 times, and preferably less than 0.8 times this thickness. This makes the surface of the passivation layer even flatter, which reduces further the risk that a crack will form in the passivation layer when mechanical stresses are present in the chip. Therefore, the electrical component has an even longer service life.

It is advantageous for the first conductor track layer to be made of metal, preferably of aluminum, and for the second conductor track layer to be made of a doped semiconductor material, preferably polysilicon. The conductor tracks that are made of aluminum have good electrical conductivity. Since aluminum has relatively low corrosion resistance, the first conductor track layer, which is close to the surface, is only provided outside of the area of the chip covered by the interaction surface, and it is located at a distance to this area. Within the area of the chip covered by the interaction surface, only the conductor track layer(s) that is (are) made of polysilicon is (are) used to locate the conductor tracks. The chip therefore has even better corrosion resistance to a liquid or viscous medium located in the opening. Outside of the chip area that is covered by the interaction surface, the polysilicon conductor tracks may be connected to the aluminum conductor tracks. At least one additional conductor track layer of metal and the least one insulation layer allocated to this conductor track layer may perhaps be disposed between the first conductor track layer and the second conductor track layer, in other words, the second conductor track layer does not necessarily need to be the conductor track layer that is second from the top, and the second insulation layer does not necessarily need to be the installation layer that is second from the top of the sensor and/or actuator chip.

In a preferred embodiment of the invention, a structure for an electronic switch, in particular for an evaluation device, is disposed on the substrate outside of the area covered by the opening, and said structure is electrically connected to the sensor and/or actuator structure by means of at least one of the conductor track layers. The switching apparatus that is comprised of the electronic circuit and the sensor and/or actuator then allows particularly compact dimensions. Moreover, the switching apparatus may be manufactured economically in standard production using semiconductor manufacturing methods.

BRIEF DESCRIPTION OF THE DRAWINGS

Examples of embodiments of the invention are explained further below based on the drawing. The drawing shows.

DESCRIPTION OF THE PREFERRED EMBODIMENTS

Figure 1:
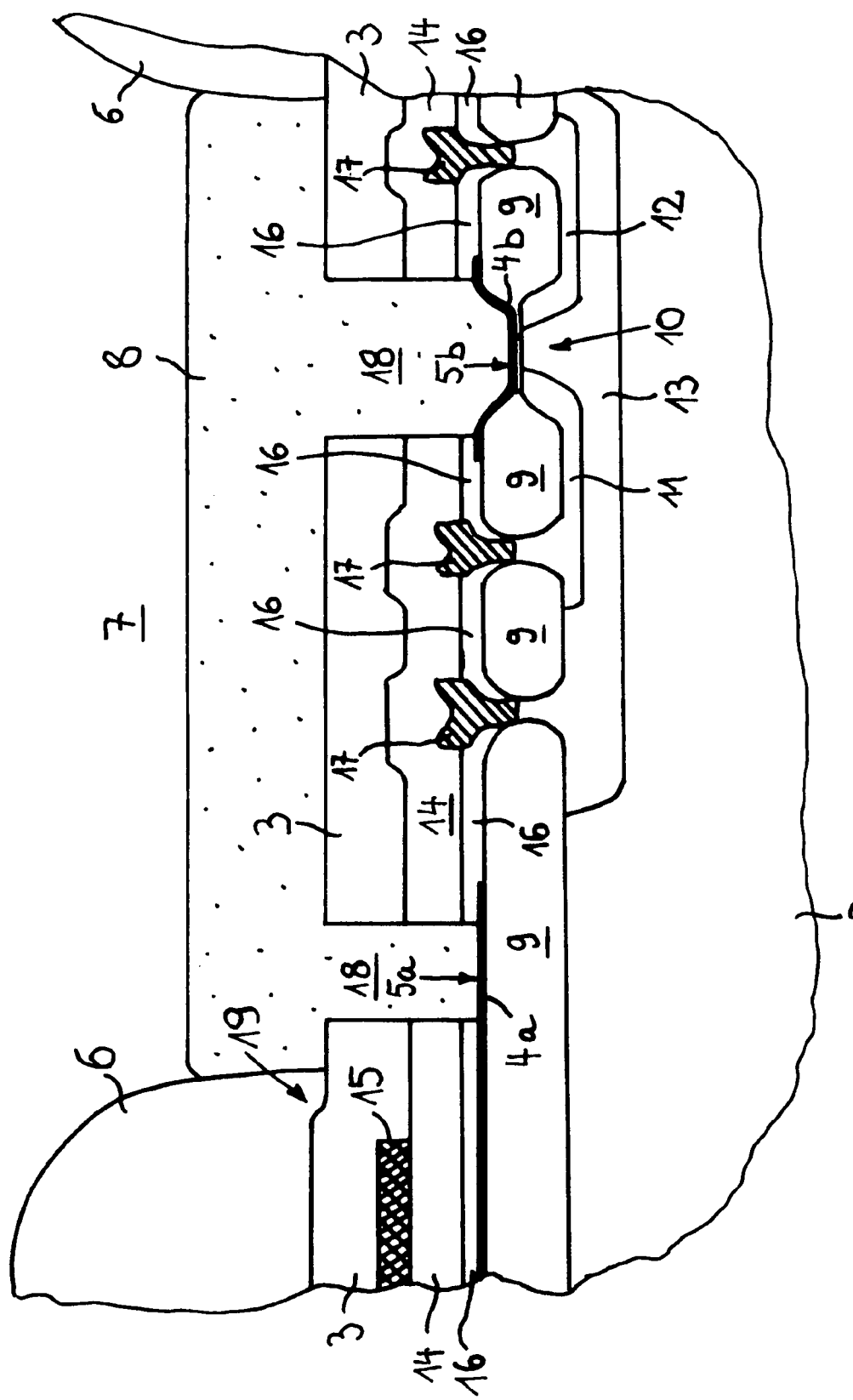
FIG. 1 is a partial cross-sectional view through a first example of an embodiment of the electrical component of the invention.

An electrical component that is identified in its entirety in FIG. 1 by the reference number 1 has a sensor chip, which has a semiconductor substrate 2 of p-doped silicon, on which structures for sensors are disposed. As a cover layer, the sensor chip has a passivation layer 3 that is preferably comprised of silicon nitride and silicon oxide and that can be several 100 nm to a few μm thick. A sensor structure shown on the left side of FIG. 1 has a precious metal electrode 4*a* with an active surface area 5*a*, and a sensor structure shown on the right side in FIG. 1 has a silicon nitride layer 4*b* with an active surface area 5*b*. The chip is surrounded by an encapsulation 6 that is formed by a casting compound and that is only partially shown in FIGS. 1 and 2. The encapsulation has an opening 7 which forms an access to the active surface areas 5*a*, 5*b*. At least the edge of the encapsulation 6 that surrounds the opening contacts the chip and performs a sealing function. A liquid or viscous medium 8 that is to be tested and that contacts the chip at an interaction surface that corresponds to the entire free surface area of the chip 1 that is shown in the embodiment example shown in FIG. 1 and that covers the opening can be placed in the opening 7. However, it is also conceivable that the interaction surface only extends across part of the surface area of the chip 1 that is covered by the opening 7, for example when the chip is only partially immersed in a liquid medium 8.

In the example of the embodiment shown in FIG. 1, the electrode 4*a* is disposed on a field oxide layer 9 provided on the substrate 2. The electrode 4*b* is configured as a gate electrode disposed adjacent to a channel area 10 of a field effect transistor (FET). The channel area 10 is formed between a p+ source 11 and a p+ drain of the field effect transistor in an n− doped area 13 that is recessed into the substrate 2. In FIG. 1 one can see that the source 11 and the drain 12 are located in area 13. On both sides of the channel area 10 the field oxide layer 9 is located on the source 11 and on the drain 12. The field oxide layer 9 has an interruption in the vicinity of the channel area 10. This is bypassed by the electrode 4b.

A first electrical insulation layer 14 is located between the passivation layer 3 and the substrate 2. It constitutes an inter-metallic dielectric (IMD). In some areas between the passivation layer 3 and the first insulation layer 14, a first conductor track layer 15, which is made of aluminum, is provided. The first conductor track layer 15 has a plurality of areas configured as conductor tracks. An inter-layer dielectric (ILD), which serves as a second electrical insulation layer 16, is located between the first insulation layer 14 and the substrate 2.

A second conductor track layer 17 is provided between the first insulation layer 14 and the second insulation layer 16. It is made of aluminum and has areas configured as conductor tracks. As can be seen in FIG. 1, a first conductor track of the second conductor track layer 17 is connected to the n-doped area 13, a second conductor track is connected to the source 11, and a third conductor track is connected to the drain 12. Interruptions are provided in the second insulation layer 16 and the field oxide layer. They are interspersed in each case with a section of the conductor tracks. The first insulation layer 14 and the second insulation layer 16 have interruptions 18 on the active surface areas 5a, 5b, of the electrodes 4a, 4b. These interruptions communicate with the opening 7 in the encapsulation 6. The second conductor track layer 17 is laterally spaced apart from the interruptions 18 by the insulation layers 14, 16, and is sealed relative to said insulation layers. The passivation layer 3 is interspersed with the interruptions 18.

In FIG. 1 one can see that the first conductor track layer 15 is located completely outside of the area of the chip that is covered by the opening 7 in the encapsulation 6. Moreover, the first conductor track layer 15 is laterally separated from the interruptions 18 by the first insulation layer 14 and by the passivation layer 3 and is sealed relative to said interruptions. It can be clearly seen that the first conductor track layer 15 in the area of the chip covered by the opening is spaced apart from the opening 7, in a direction that is normal to the plane of extension of the chip, by the passivation layer 3 and the first insulation layer 14 located beneath it. Good corrosion resistance is thereby achieved for the first conductor track layer 15 relative to the medium 8 located in the opening 7. The surface of the passivation layer 3 that borders the opening 7 is largely flat in the areas that are separated by the interruptions 18, so that the risk of a crack forming in the passivation layer 3 is reduced accordingly when mechanical stresses occur in the chip. A shoulder 19 in the passivation layer 3 caused by the first conductor track layer 15 on an area of the surface of the passivation layer 3 facing away from the substrate 2 is covered by the encapsulation 6 and is separated laterally from the opening 7. Thus, if a crack in the passivation layer happens to form at the shoulder 19, the second conductor track layer 17 is largely sealed off from the opening 17 by the encapsulation 6 and is thus protected from corrosion caused by the medium 8.

The electric component 1 shown in FIG. 1 therefore has a sensor and/or actuator chip with a substrate 2 on which a passivation layer 3 and a sensor and/or actuation structure having an active surface region 5a, 5b are disposed. The chip is surrounded by an encapsulation 6 that has an opening 7 that forms an access to the active surface area 5a, 5b, of which there is at least one. A stack of layers is located on the substrate 2; beginning with the passivation layer 3 and extending to the substrate 3, it has at least one first conductor track layer 15, one first electrical insulation layer 14, one second conductor track layer 17, and one second electrical insulation layer 16. The first conductor track layer 15 is located completely outside the area of the chip that is covered by the opening 7. At least one conductor track of the second conductor track layer 15 is connected to the sensor and/or actuator structure.

Figure 2:
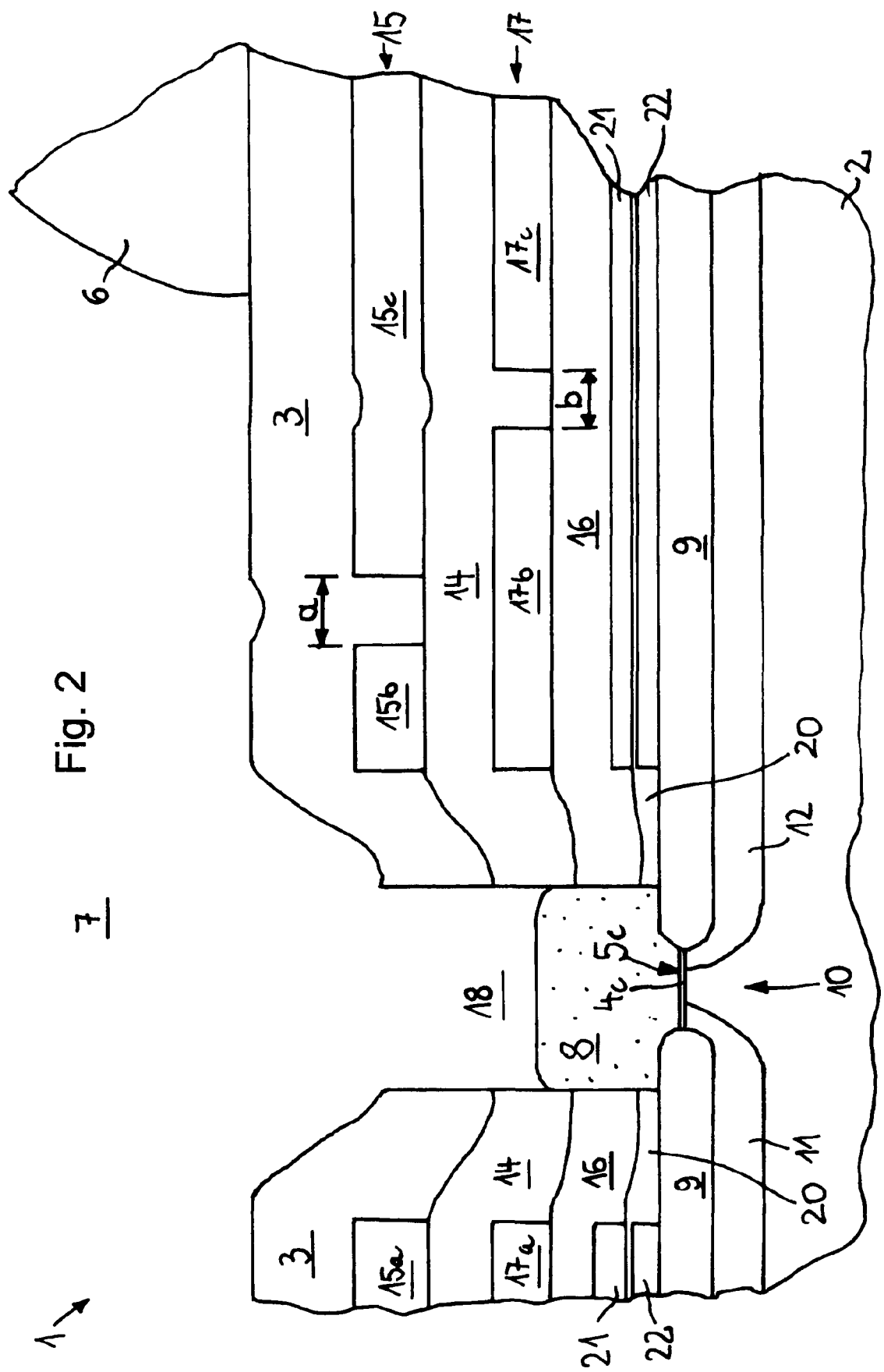
FIG. 2 shows a partial cross-sectional view through a second example of an embodiment of the component of the invention.

In the example of an embodiment shown in FIG. 2, a field effect transistor having a source 11, a drain 12, and the channel area 10 is integrated into the substrate 2. Adjacent to the channel area 10 the field effect transistor has a gate electrode 4c with an active surface area 5c. With the aid of the field effect transistor it is possible, for example, to detect ions located in a medium 8 that is present in the opening and that is in contact with the gate electrode 4c. A field oxide layer 9, which has an interruption that is adjacent to the channel area 10 and that is bypassed by the gate electrode 4c, is located at the source 11 and at the drain 12.

In this example of an embodiment a first electrical insulation layer 14 is also located between the passivation layer 3 and the substrate 2. It constitutes an inter-metallic dielectric (IMD). A first conductor track layer 15, which is made of aluminum and has a plurality of electrically conductive layer areas 15a, 15b, 15c, is provided in some areas between the passivation layer 3 and the first insulation layer 14. The layer areas 15a, 15b are configured as conductor tracks. Layer area 15c is not used as a conductor track. In the area of the first conductor track layer 15 that is covered by the opening 7 and the passivation layer 3, the distances a between the layer areas 15a, 15b, 15c, which are laterally adjacent to each other, in each case are less than the thickness of the conductor track layer 15.

An inter-layer dielectric (ILD), which functions as a second electrical insulation layer 16, is disposed between the first insulation layer 14 and in the substrate 2. A second conductor track layer 17, which is made of aluminum, is disposed in some areas between the first insulation layer 14 and the second insulation layer 16. The second conductor track layer 17 and the first insulation layer 14 are interspersed with the interruption 18. The second insulation layer 17 ends at a distance to the interruption 18 and is sealed off from the interruption 18 by the first insulation layer 14 and the second insulation layer 16.

The second conductor track layer 17 has a plurality of electrically conductive layer areas 17a, 17b, 17c. Layer areas 17a, 17b are configured as conductor tracks, while layer area 17c is not used as a conductor track. In the area of the second conductor track layer 17 covered by the opening 7 and the passivation layer 3, the distances b between the laterally adjacent layer areas 17a, 17b, 17c are each less than the thickness of the conductor track layer 17. This thickness more or less corresponds to the thickness of the first electrical insulation layer 14, the first conductor track layer 15, and the passivation layer 3. Because of the small lateral distances a, b between the layer areas 15a, 15b, 15c of the first conductor track layer 15 or the layer areas 17a, 17b, 17c of the second conductor track layer 17, the areas of the surface of the passivation layer 3, which correspond to the orthogonal projection of the spaces between the layer areas 15a, 15b, 15c, 17a, 17b, 17c of a conductor track layer 15, 17, which are arranged adjacent to each other, are largely flat. As a consequence, the risk that a crack will form in the passivation layer 3 when mechanical stresses are present in the chip is reduced accordingly.

A third electrical insulation layer 20, which is embodied as an oxide layer, is disposed between the second insulation layer 16 and the field oxide layer 9. In some areas a third conductor track layer 21, which is comprised of a polysilicon layer and which forms conductor tracks, is located between this insulation layer and the second insulation layer 16. A fourth conductor track layer 22 is located between the third insulation layer 20 and the field oxide layer 9. It is also made of a polysilicon layer 22 and has further electrical conductor tracks.

It must also be noted that the conductor tracks in conductor track layers 15, 17, 21, 22 may be connected to each other by means of through-contacts. The substrate 2 may also be made of glass.

The invention claimed is:

1. An electrical component having a sensor and/or actuator chip, in particular a CMOS chip, that has a substrate on which a passivation layer and at least one structure that has at least one active surface area for a sensor and/or actuator is located, and the chip is surrounded by an encapsulation that has at least one opening that forms an access to the active surface area and to the passivation layer, and in the opening the chip has an interaction surface that extends, at least in some areas, atop of the passivation layer and the active surface area and that in operation the interaction surface is in contact with a liquid or viscous medium, and a first electrical insulation layer is provided between the passivation layer and the substrate, and a first conductor track layer that has at least two laterally separated electrically conductive layer areas is located in some areas between the passivation layer and the first insulation layer, and a second electrical insulation layer is provided between the first insulation layer and the substrate, and a second conductor track layer is located between the first insulation layer and the second insulation layer, wherein at least in the area of the first conductor track layer that is covered by the interaction surface a distance between the laterally adjacent, electrically conductive layer areas in each case is smaller than 1.2 times the thickness of this conductor track layer.

2. The electrical component of claim 1, wherein, at the least in the area of the first conductor track layer covered by the interaction surface, the distance between the laterally adjacent areas of this conductor track layer in each case is either: less than 1.1 times the thickness of the first conductor track layer; less than 1.0 times the thickness of the first conductor track layer; less than 0.9 times the thickness of the first conductor track layer; or less than 0.8 times the thickness of the first conductor track layer.

3. The electrical component of claim 1, wherein the second conductor track layer has at least two laterally separated electrically conductive layer areas, wherein at least in the area of the second conductor track layer covered by the interaction surface, the distance between the laterally adjacent areas of this conductor track layer in each case is either: less than 1.2 times the thickness of the first conductor track layer; less than 1.1 times the thickness of the first conductor track layer; less than 1.0 times the thickness of the first conductor track layer; less than 0.9 times the thickness of the first conductor track layer; or less than 0.8 times the thickness of the first conductor track layer.

4. The electrical component of claim 1, wherein the first conductor track layer is comprised of metal, preferably aluminum, and the second conductor track layer is comprised of a doped semiconductor material, preferably polysilicon.

5. The electrical component of claim 1, wherein a structure for an electronic circuit, in particular a structure for an evaluation device, is located on the substrate outside of the area covered by the opening, and said structure is electrically connected to the sensor and/or actuator structure by means of at least one of the conductor track layers.

6. The electrical component of claim 1, wherein the interaction surface does not include any area of either the first conductor track layer, the second conductor track layer, or both.

* * * * *